United States Patent [19]

Blum

[11] 4,259,079

[45] Mar. 31, 1981

[54] METHOD AND APPARATUS FOR ELECTRICAL SEPARATION OF MOLECULES

[76] Inventor: Alvin S. Blum, 2350 Del Mar Pl., Fort Lauderdale, Fla. 33301

[21] Appl. No.: 972,670

[22] Filed: Dec. 26, 1978

Related U.S. Application Data

[63] Continuation of Ser. No. 898,998, Apr. 21, 1978.

[51] Int. Cl.³ ...................... G01N 33/56; G01N 35/08
[52] U.S. Cl. ................................. 23/230 R; 23/230 B; 23/920; 204/180 G; 422/81; 422/82; 435/291
[58] Field of Search ................. 23/230 R, 230 B, 920; 422/81, 82, 72; 356/197, 246; 204/180 G

[56] References Cited

U.S. PATENT DOCUMENTS

| | | | |
|---|---|---|---|
| 3,320,148 | 5/1967 | Skeggs | 422/82 X |
| 3,320,149 | 5/1967 | Isreeli | 422/82 X |

Primary Examiner—Ronald Serwin

[57] ABSTRACT

Method and apparatus for analysis of certain molecules in the presence of other molecules in a flowing stream which comprises:

Controlled dispensing of sample and reagents into a flowing stream; novel electrical separation apparatus; separation of certain molecules in said sample stream into other streams by said separation means; and means for serially measuring properties of said separated molecules for quantitation of the original sample.

18 Claims, 9 Drawing Figures

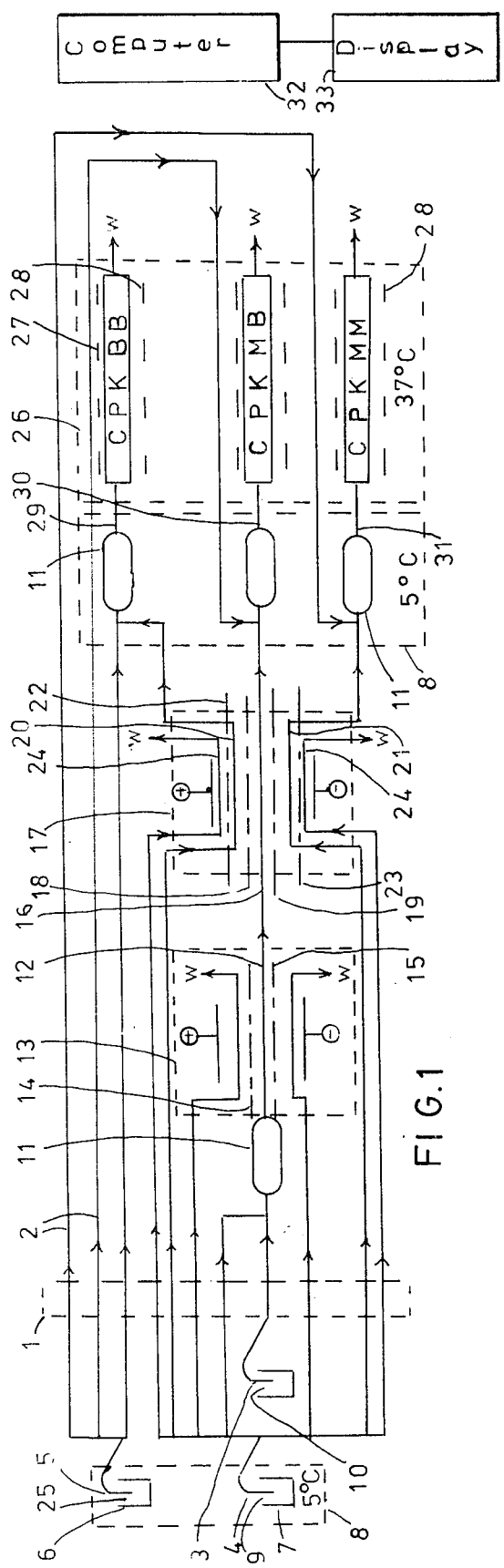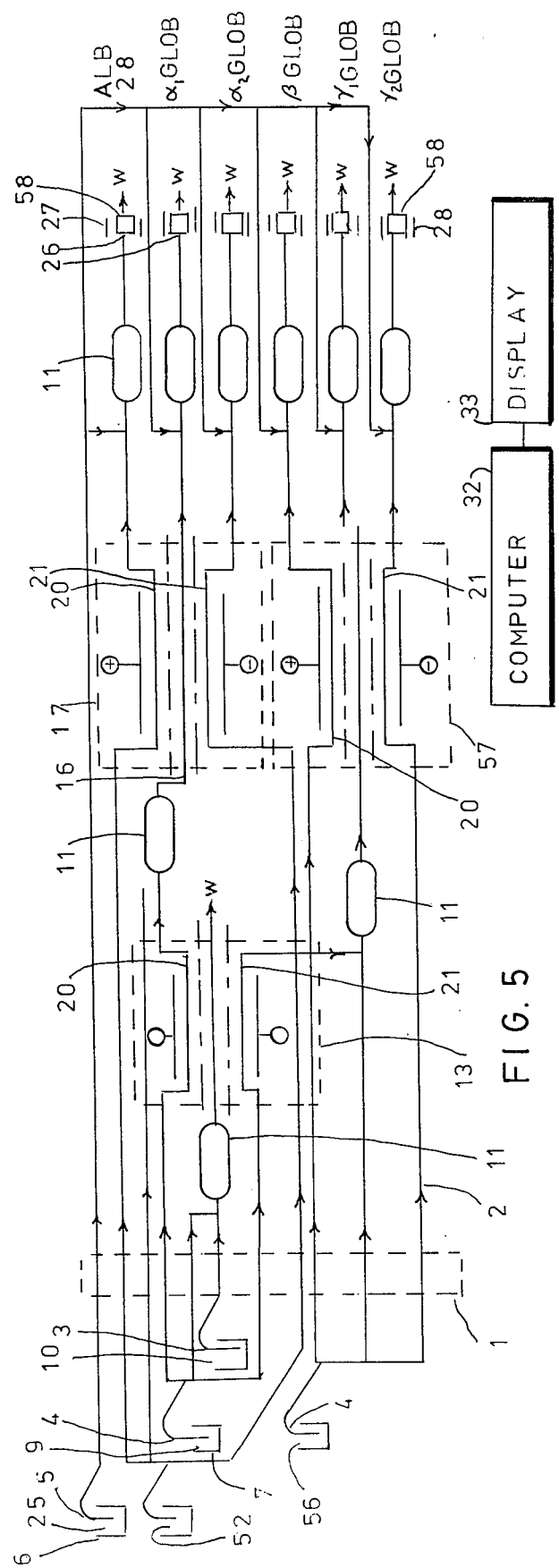
FIG. 1
FIG. 5

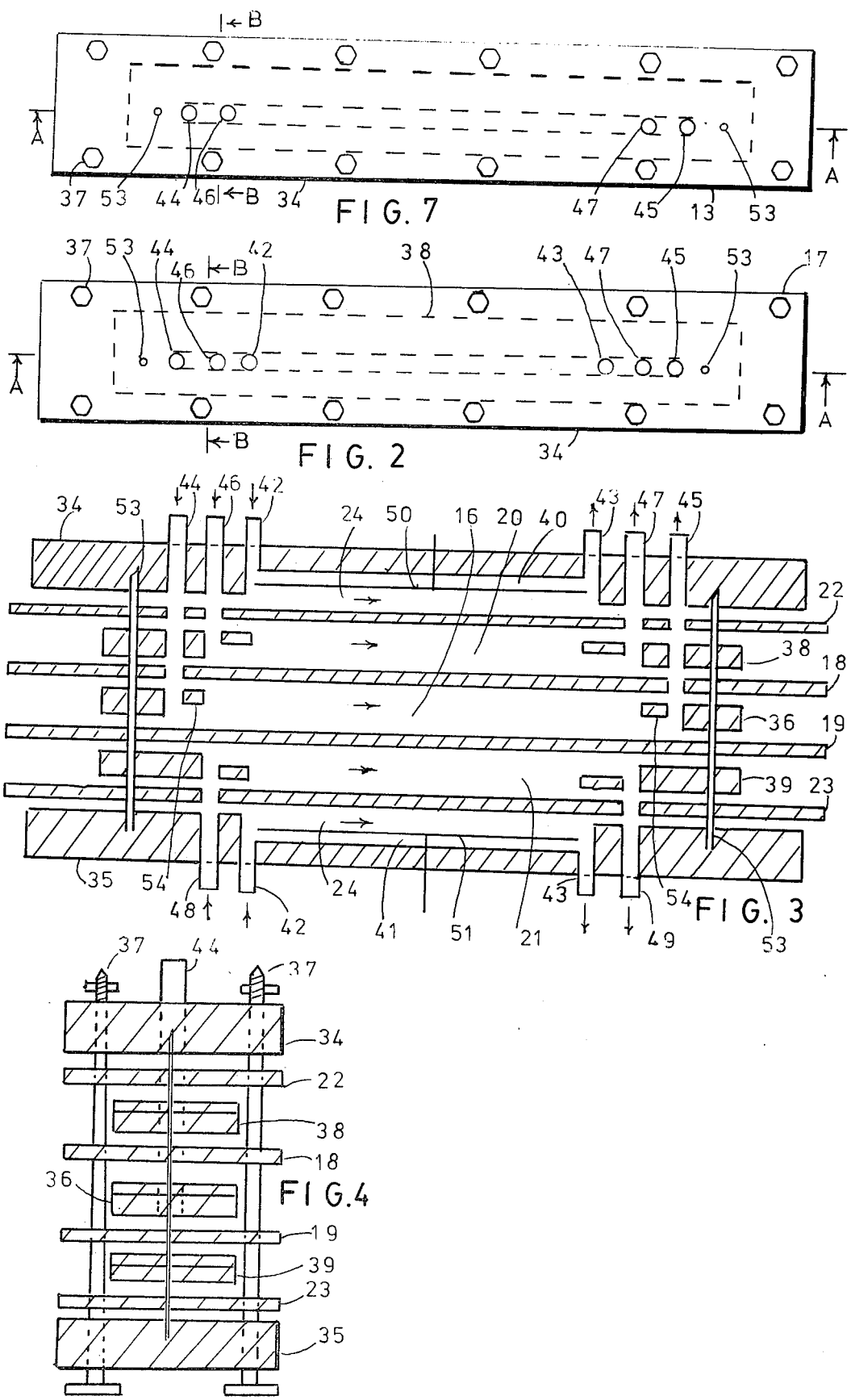

METHOD AND APPARATUS FOR ELECTRICAL SEPARATION OF MOLECULES

This is a continuation-in-part of application Ser. No. 898,998 filed Apr. 21, 1978.

BACKGROUND OF THE INVENTION

1. Field of the Invention

The invention relates to method and apparatus for analyzing mixtures of molecules such as serum proteins, or free antigen and antibody bound antigen as in competitive binding analysis, or isoenzymes.

Competitive binding analysis

The invention relates to a method and apparatus for analyzing the concentration of a substance in a sample liquid by the technique of competitive binding analysis, a currently important subdivision of which is radioimmunoassay. The technique involves the combining of the substance to be measured (ligand) with a specific binding agent. The ligand is often an antigen and the binding agent an antibody thereto. The extent of the reaction is measured by a label or tracer, usually radioactive, but tracer may also be, for example, fluorescent or an enzyme. The present invention relates in particular to methods and apparatus permitting such analysis to be made more rapidly by machine with a minimum of labor and error.

Isoenzymes

Isoenzymes are multiple molecular forms of an enzyme which catalyze the same reaction, buf differ in certain physical chemical properties, such as electrophoretic mobility. Following electrophoresis five isoenzymes of lactic dehydrogenase (LDH) and three isoenzymes of creatine phosphokinase (CPK) have been demonostrated in human serum. Each isoenzyme of LDH is designated by a number related to its electrophoretic mobility. The fastest moving fraction (most anodic) is designated LDH 1 and is found primarily in heart muscle. The slowest moving (most cathodic) is LDH 5 and is found primarily in liver and skeletal muscle. The others LDH 2, LDH 3 and LDH 4 are found to varying degrees along with LDH 1 and LDH 5 in all tissues.

2. Description of the Prior Art

Competitive binding analysis

Yalow and Berson (Nature 1 84,1648,1959) introduced a new analytical method for assaying the minute amounts of insulin found in the blood. An antibody to insulin was mixed with the sample plus a known amount of radioactive insulin. The total concentration of insulin exceeded the binding capacity of the antibody. At equilibrium, when all the antibody was bound to either radioactive insulin or nonradioactive insulin, the antibody bound insulin was separated from the free insulin by membrane electrophoresis and the radioactivity in each portion measured. By means of standards a relationship was established between the ratio of bound to unbound radioactivity and the amount of insulin in the sample. Because the general analytical principle of the method is so exquisitely sensitive and specific for biologically important molecules that are difficult to analyze by other means, the method has grown and diversified into an important clinical procedure.

Specific binding agents now include cell membrane receptors, tissue receptors, naturally occurring specific binding agents such as the transins as well as the more common antibodies.

Ligands include elements, peptide hormones, steroid hormones, proteins, virus and tumor components. In addition to radioactive labeling we also find fluorescent and other optical labels and enzyme labeling. In those cases where the binding agent is the analyte, a constant amount of ligand is employed.

Separation methods include: differential migration of bound and unbound ligand such as gel filtration, chromatography, zone electrophoresis; isolation of unbound ligand by adsorbtion on coated charcoal, silica, talc; isolation of bound ligand by double antibody precipitation, salt precipitation, ethanol precipitation, dialysis. The Skeggs (U.S. Pat. No. 2,797,149) continuous dialysis and the Ferrari (U.S. Pat. No. 3,211,645) continuous filtration techniques have not been employed for this separation. Solid phase systems employing binding agent affixed to test tube wall, beads or column packing have become popular.

Because of the increase in the volume and applications of this technique to clinical medicine, recent attention in this area has centered on automatic and semiautomatic systems for performing these analyses. Many of these are adaptations of the continuous chemical analyzer of Skeggs (U.S. Pat. No. 2,797,149). These include the devices marketed by Technicon Corp. which use magnetic retention of iron coupled antibody. Also the Brooker (U.S. Pat. No. 4,022,577) method of dynamic measurement of total radioactivity followed by a second static measurement of one separated component. Also the Johnson (U.S. Pat. No. 3,896,217) method of separation with alternate adsorbtion and elution of one component on a column containing antibody fixed to the column packing for efficient reutilization of antibody. A need exists for a technique which combines automation with simplicity, versatility and greater throughput rate for samples.

Enzymes

Enzyme analyses are generally performed in solution by spectrophotomeric or fluorometric measurements under controlled conditions of the disappearance or appearance of a substrate or its metabolite. Isoenzymes can be separated by column chromatography and the enzyme concentration of the eluates determined by such means. However these procedures have been shown to have poor precision and accuracy and to be fraught with problems of interpretation. They are also time consuming. In current clinical practice, isoenzymes are generally analyzed by first performing electrophoretic separation of the serum on a cellulose acetate or agarose support strip in an electric field in a suitable buffer for 10 minutes. The strip containing the separated isoenzymes is then sandwiched against a second strip holding the appropriate reagents to visualize either CPK or LDH after 25 minutes incubation. The strip is then dried and quantitated by a scanning fluorescent densitometer. 13 (CPK) or 20 (LDH) individual skilled steps are necessary before the strip is ready for the densitometer. The automatic densitometer costs $3750 to $6000 and a computer to assist its somewhat complex operation costs at least $3000. A considerable effort and time of a skilled operator is required for these densitometric measurements.

There may be other interfering enzymes or agents in the serum which may react to give false readings of the desired enzyme. It is expected that other isoenzyme analyses may prove useful in the future when suitable methods and data become available.

It is difficult to provide at all hours the skilled staff required to perform these analyses. With all the other duties charged to the laboratorian, such time consuming procedures cannot be performed on the stat basis that many patients' condition dictates. The present procedures are so awkward and involve so many steps and variables that they are quite imprecise even in the best of hands. A need exists for a technique which combines automation with simplicity, versatility, precision, and rapid throughput for stat samples that will be available for use by relatively unskilled persons at all hours with little operator time.

SUMMARY OF THE PRESENT INVENTION

An object of the present invention is to provide novel method and apparatus for the separation of a large molecule in a continuously flowing stream and more particularly bound ligand from unbound ligand while retaining the bubble separation means of Skeggs. Ligands are generally small, of molecular weight several hundred or less. Binding agents are generally large in size with molecular weights of tens of thousands or more. They often also have a smaller electrical charge to mass ratio. Consequently, after incubation of ligand and binding agent, we find two kinds of ligand, a small charged form and a very large form with lesser charge. This invention provides novel apparatus of simple and inexpensive construction to separate these two forms which comprises: a central channel through which flows the mixture of bound and unbound ligand; at least one additional parallel recipient flow channel adjacent the central channel and separated therefrom along its length by a semipermeable membrane of sufficient permeability to allow passage of the unbound ligand. The membrane need not be completely impermeable to the bound ligand. Electrodes in at least two of the channels with electric potential applied thereto. The electric potential applies a driving force to the charged molecules or ions. The unbound ligand with a greater charge to mass ratio than the bound ligand, experiences a greater driving force across the membrane. Being of much smaller size it moves through the solution more rapidly. Being of much smaller size, it passes through the semipermeable membrane more readily. The combination of all of these factors favors the movement of the unbound ligand over the bound ligand from the central channel to the recipient channel, resulting in the separation of the bound ligand in the central channel and the unbound ligand in the recipient channel. The extent of the separation will be influenced by the distance the unbound ligand must travel to reach the recipient stream. In a preferred embodiment a very thin, less than one millimeter, central channel is sandwiched between two parallel contiguous channels and separated therefrom by two semipermeable membranes. Each of the recipient channels contains an electrode. The electric field extends from the first recipient channel, across the first membrane, across the smallest dimension of the central channel, across the second membrane, to the electrode in the second recipient channel. All of the charged particles will tend to move out of the central channel in response to the electric field. A loss of ions may alter the composition of the incubated mixture unfavorably. For example, the ionic strength or acidity may change so much that ligand binding may be disrupted. By providing an ion containing stream on either side of the central channel, a charged particle from one recipient channel will tend to enter the central channel for every particle of like charge which leaves the central channel to the opposite recipient channel. This tends to stabilize the composition of the central channel. The flow rate through the recipient channels may be much greater than through the central to provide a surplus of ions and to wash away received ligand that has moved across by electric forces or by dialysis. In some cases dialysis may provide a considerable portion of the separation, it takes place independent of the electric forces. The length of said central channel is very great relative to the distance across said membranes so that the unbound ligand is exposed to the electric force for a prolonged period and the distance it must migrate for separation is very short.

Another object of the present invention is to provide an apparatus and method for automatic isoenzyme analysis that is simple to operate, relatively foolproof, reliable, consistent, direct reading, fast action, conservative of expensive reagents, available at all hours, fast easy changeover from one enzyme to another so that on a single sample it becomes practical to perform CPK and then LDH instead of batching multiple samples and running CPK on all of them and then changing to LDH. It is a further object of the invention that new enzyme assays are easily added to the repertory. It is a further object that automatic means be provided for removing interfering materials from the sample to improve enzyme analysis. It is a further object that means be provided for separating the isoenzymes into separate moving streams. It is a further object that means be provided for admixing reagents with said streams of separated enzymes. It is a further object that means be provided to control temperature of said mixtures. It is a further object that means be provided to measure changes in optical properties of said mixtures. It is a further object that data processing means be provided to convert optical measurements into useful data readout. It is a further object of the invention that it provide a wide range of sensitivities so that very low values can be measured and very high values can also be measured before reagent is exhausted and require dilution and repeat analysis.

Another object of the present invention is to provide novel method and apparatus for the separation, in a moving fluid stream, of a particular type of molecule from other types of molecules on the basis of certain differences in their physical chemical properties. This invention provides simple and inexpensive electroextraction means to separate said molecules which comprises: a central channel through which flows the mixture of molecules to be separated; at least one additional parallel recipient flow channel adjacent the central channel and separated therefrom along its greater length by a membrane sufficiently permeable to allow passage of at least one of the types of molecules to be separated; electrodes in at least two of the channels with a difference of electric potential applied thereto, said potential applying a driving force to molecules having a net electric charge of either sign, thereby moving said molecule from one channel to another. The extent of the separation will be influenced by the distance the charged molecule must travel to reach the recipient stream. In a preferred embodiment, a very thin (less than 1 millimeter) central channel is sandwiched between two parallel contiguous recipient channels and separated therefrom by two membranes permeable to the appropriate molecules. Each of the recipient channels contains an electrode. The electric field extends from the first recipient channel, across the first membrane, across the small dimension of the central channel, across the second membrane, to the electrode in the second recipient channel. All of the charged molecules will tend to move out of the central channel in response to the electric field. A loss of ions may alter the composition of the mixture in the central channel adversely. For example, the ionic strength or pH may change so much as to disrupt certain bonds. By providing an ion containing stream on either side of the central channel, a charged particle from one recipient channel will tend to enter the central channel for every particle of like charge which leaves the central channel for the opposite recipient channel. This tends to stabilize the composition of the central channel fluid. The flow rate through the recipient channels may be much greater than through the central channel to provide a surplus of ions and to wash away received molecules that have migrated across the membranes by electric forces or dialysis. Dialysis takes place independent of electric forces. The length of said central channel may be very great relative to the distance between membranes so that molecules are exposed to the electric force for a prolonged period, and the distance they must migrate is short.

It may be desirable in certain situations to stabilize the composition of the recipient streams or limit their flow. This is facilitated in another embodiment of the present invention wherein each electrode is in its own flow channel, separated from its recipient channel by another membrane.

Amphoterism is a property of amino acids, polypeptides, proteins (of which enzymes are a class), and many other clinically important constituents of body fluids. Ampholytes (amphoteric electrolytes) dissociate both as acids and as bases depending upon the pH of the solution. If an ampholyte in solution is placed in an electric field, the molecules will migrate to one electrode or the other in accordance with the pH of the solution. At a given pH, the molecule behaves neither as an acid nor as a base and does not migrate to anode or cathode. This is called the isoelectric point. It is usually expressed in terms of the pH of the solution at which this occurs. In the isoelectric state the ampholyte is thought to be dissociated both as an acid and as a base and fails to appear electrically charged because its positive and negative charges are equal i.e. net charge is zero. When acid is added the ampholyte behaves as a base with a net positive charge; when alkali is added, it behaves as an acid with a net negative charge.

It is an object of the present invention to control and select the migration and separation of different molecules by adjustment of the pH of the streams moving through the electroextraction means. It is a further object of the present invention that means be provided to analyze a plurality of different molecules simultaneously using a plurality of said electroextraction means and serial adjustment of pH of the moving streams.

The foregoing and other objects of the present invention will be described more fully in the following detailed descriptions of the invention.

BRIEF DESCRIPTION OF THE DRAWINGS

FIG. 1 is a schematic drawing of apparatus of the type to which the invention relates showing sample, buffer and reagent being aspirated into an automatic isoenzyme analyzer with a first electroseparation stage removing interfering agents, a second electroseparation stage separating CPK into MM, MB, and BB fractions, color development with reagent, and serial optical measurement of color developing in each separated stream.

FIG. 2 is a top plan view of the electrical separation apparatus having separate electrode flow channels.

FIG. 3 is a cross section, thru line A—A' of FIG. 2.

FIG. 4 is a cross section, thru line B—B' of FIG. 2.

FIG. 5 is a schematic diagram of apparatus of the type to which the invention relates showing an automatic serum protein analyzer.

FIG. 7 is a top plan view of the electrical separation apparatus having electrodes within the recipient channels.

DESCRIPTION OF THE PREFERRED EMBODIMENTS

Figure 6:
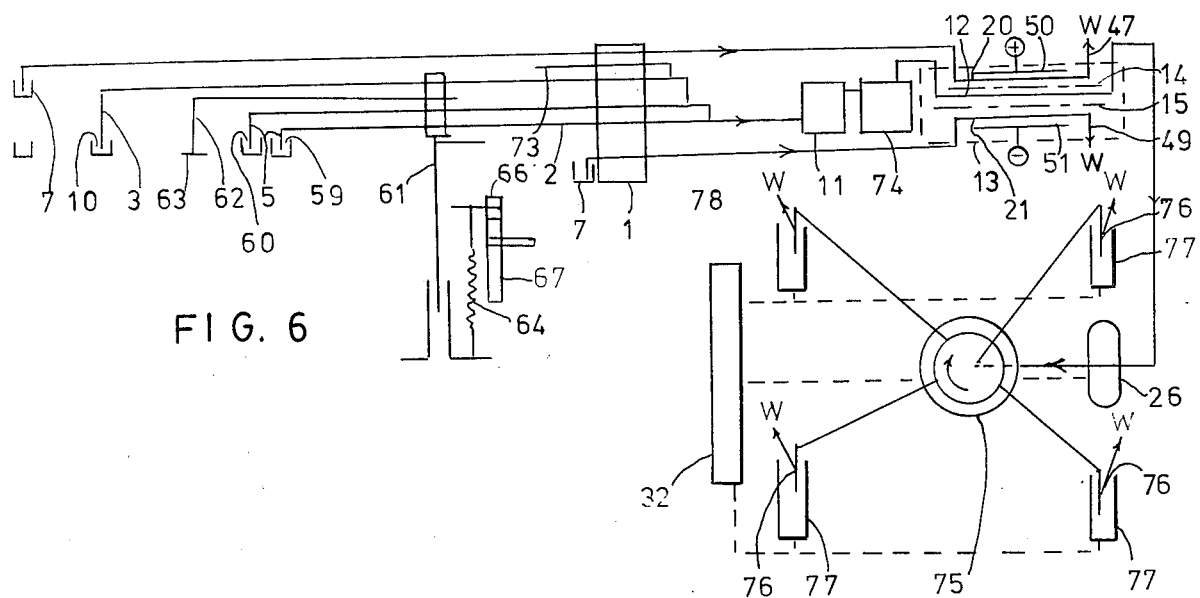
FIG. 6 is a schematic drawing of apparatus of the type to which the invention relates showing an automatic competitive binding analyzer embodying the electrical separation means with electrodes within the recipient channels.

Referring first to FIG. 1, peristaltic proportioning pump means 1 pulls fluid at precise rates through flexible tubing lines 2 metering the fluids. Three of these lines terminate in sample pipet 3, buffer pipet 4, and reagent pipet 5, shown immersed in their respective liquids in individual containers. Reagent container 6 and buffer container 7 are held at reduced temperature, by temperature control means 8. Isoenzyme analysis is carried out by addition of buffer 9 to the sample 10 and mixing in mixing coil 11. This adjusts sample pH to the isoelectric point of the CPKMB fraction just before it moves through the central channel 12 of first separation means 13. Membranes 14 and 15 are of a pore size too small to allow passage of the enzymes. Charged molecules small enough to pass through the membranes 14 and 15 are removed by the electrophoretic process and by dialysis which also can remove uncharged molecules at a reduced rate. This process improves final analysis by removal of interfering materials. This partially purified stream enters central channel 16 of second separation means 17 at the isoelectric point of CPKMB. At this pH, the MM fraction is positively charged and migrates toward the cathode. The BB fraction is negatively charged and migrates toward the anode. Membranes 18 and 19 are of a porosity great enough to allow passage of enzyme MM into recipient channel 21 and BB into recipient channel 20. Membranes 22 and 23 have such small porosity as to exclude the enzymes from the electrode channels 24. Major changes in fluid composition from electrode effects are thereby restricted to the electrode channels. The other three channels have as many charged molecules leaving as entering so that their composition is relatively stable. The MB fraction passes through the central channel. Color forming enzyme substrate reagent 25 is pumped and mixed with each of the three separated streams in mixing coils 11 maintained at low temperature to reduce substrate depletion during mixing. The three mixed, cooled streams of enzyme and substrate next enter temperature controlled (37° C.) three channel optical detector 26 wherein optical properties, and change of optical properties with time are detected by light sources 27 and light sensors 28. These view the streams 29,30 and 31 at progressively later times after mixing of enzymes with substrate and raising to reaction temperature. Signals from the sensors are connected by wires not shown to data processing means 32 where enzyme levels of each fraction are computed and displayed on display means 33. For clarity and simplicity the foregoing description has been limited to one analysis. Additional enzymes or isoenzymes may be analyzed simultaneously by the use of parallel analysis streams. They may share a common detector and data processor, and when isoelectric points are compatible, may even share a separation means.

FIG. 2 shows a plan view of an embodiment of the electric separation apparatus, FIG. 3 is a sectional view taken on line A—A' of FIG. 2 and FIG. 4 is a sectional view taken on line B—B' of FIG. 2. Rigid and thick upper member 34 and lower member 35 and thin members 36,38 and 39 are bolted together with bolts 37 sandwiching in thin membranes 18,19,22 and 23. These drawings are not to scale. Inner members and membranes are shown much thicker than they are for clarity. Top member 34 has groove 40 on its underside terminating at tubes 42 and 43. Bottom member 35 has groove 41 on its upper surface terminating in tubes 42 and 43. Center member 36 has slot which connects with tubes 44 and 45 in top member via 2 holes in membranes. When membranes are tightly compressed by bolts, the grooves and slots are sealed so that five parallel channels are formed through which fluid may be passed. The central channel terminates at reagent mixture inlet 44 and outlet 45. Membrane 18 forms a common wall that channel 16 shares with upper recipient channel 20, and membrane 19 forms a common wall that channel 16 shares with lower recipient channel 21. Upper recipient channel 20 terminates in recipient inlet 46 and outlet 47. Lower recipient channel 21 terminates in recipient inlet 48 and outlet 49. Electrode 50 in upper electrode channel 24 and electrode 51 in lower electrode channel 24 are connected to positive and negative voltage respectively. The electrode may be a conductive layer deposited within the grooves 40 and 41. The exact nature of the applied voltage may be varied to suit requirements. In the assembly of the separator, sharp locator pins 53, fastened to lower member 35 transfix the membranes and pass through holes in members to facilitate alignment during assembly. Bolts 37 have sharpened points which pierce membranes during insertion to prevent membrane displacement. Holes are punched in members and membranes as indicated to permit fluid flow. During operation of the separator it was noted that leakage occurred between recipient channel and central channel where inlets 44 and 46 meet membrane 18. Construction of center member 36 was modified to provide the two bridges 54 between inlets 44 and 46 and outlets 47 and 45. This was easily accomplished by constructing the center member of a top and bottom piece laminated together. The bottom piece has a slot cut between holes in membrane at 44 and 45. The top piece has holes cut at 44 and 45 and a slot cut between 46 and 47, leaving bridges 54 to seal the membrane at these points. Bridges 55 in intermediate members 38 and 39 perform a similar sealing function.

A sample mixture is forced through central channel 16 via tube 44. Appropriate recipient fluids such as conductive buffers are passed through channels 20 and 21 via tubes 46 and 48. A difference of electrical potential is applied to electrodes 50 and 51 in electrode channels 24 furnished with a flow of appropriate fluid via inlet tubes 42 and outlet tubes 43. Charged molecules will migrate toward one of the electrodes as the mixture passes through channel 16. Larger molecules will migrate more slowly than smaller molecules. Membranes 18 and 19 may be selected of a porosity to be freely permeable to the molecules to be removed from central stream but to stop or retard charged molecules which must not leave said central channel. Electrode membranes 22 and 23 will be selected of a porosity to be freely permeable to small molecules, but to stop or retard those charged molecules which must be retained within the recipient channels. Appropriate selection of voltage, pH, ionic strength, and solution flow rates will regulate separation of molecules so that some will emerge from tube 45 and others from either tubes 47,49 or 43. Any or all streams may then be collected for subsequent measurement or passed thru detectors for immediate measurement. The fluid emerging at tubes 43 from electrode channels 24 will be most altered by electrode effects, whereas the other three channels tend to have as many charged molecules leaving as entering so that their composition is relatively stable and more suited to certain measurements.

Figure 9:
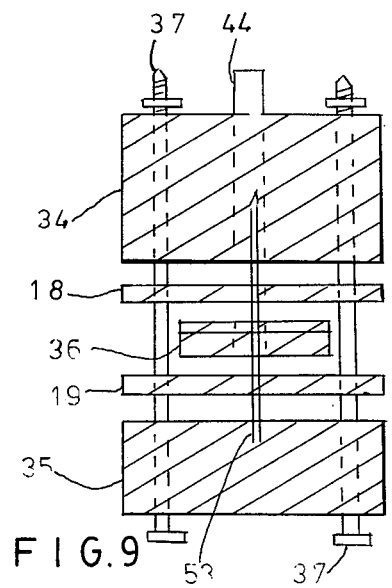
FIG. 9 is a cross sectional view taken on B—B' of FIG. 7.
Figure 8:
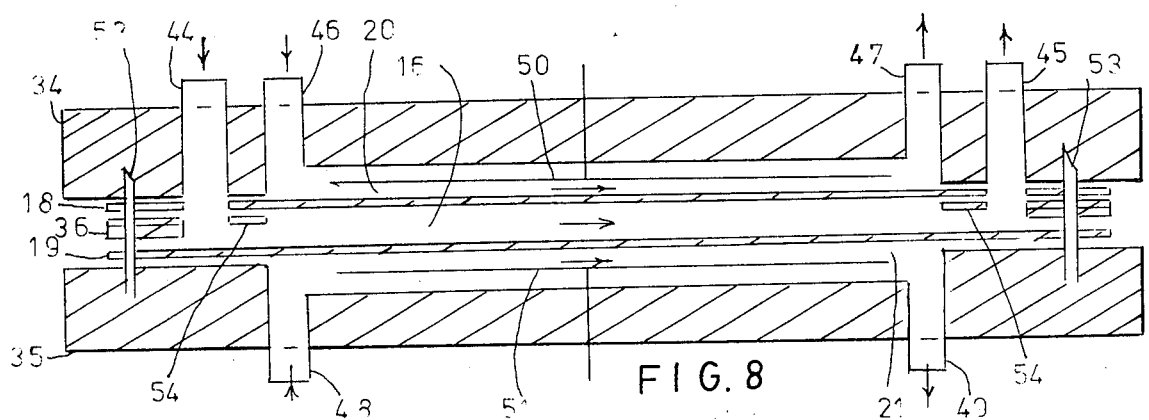
FIG. 8 is a cross sectional view taken on A—A' of FIG. 7.

FIG. 7 is a top plan view of another, more simple embodiment of the electrical separation apparatus, and FIG. 8 is a cross sectional diagram on line A-A' of FIG. 7 and FIG. 9 is a cross sectional diagram on line B—B' of FIG. 7. In this embodiment, electrodes 50 and 51 are contained within recipient channels 20, 21, separated from central channel 16 by membranes 18 and 19. This simpler embodiment is employed when electrode effects are not deleterious to recipient channel composition.

FIG. 5 shows a schematic diagram of an embodiment of the present invention for analyzing multiple molecular forms of compounds such as the analysis termed "serum protein electrophoresis." Peristaltic pump 1 of the tube pinching type in common use aspirates sample 10 and first buffer 9. They mix in mixing coil 11 bringing serum to an intermediate pH at which it enters first separator 13. The negatively charged proteins Albumin, alpha 1 globulin, and alpha 2 globulin enter anode recipient channel 20, and that stream is next mixed in mixing coil 11 with buffer 52 to reach the isoelectric point of alpha 1 globulin. This mixture passes into central channel of separator 17. Albumin, being negatively charged at this pH passes into anode channel 20. Alpha 1 globulin, having no net charge passes directly through the central channel. Alpha 2 globulin, being positively charged at the pH passes into cathode channel 21. These three streams are each combined with color developing reagent 25 in heated mixing coils 11 and then pass through optical detectors 26. The positively charged proteins, beta globulin, gamma 1 globulin, and gamma 2 globulin in first separator 13 enter cathode recipient channel 21. They are then mixed in mixing coil 11 with buffer 56 to reach the isoelectric point of gamma 1 globulin. This mixture next passes into the central channel of separator 57. Beta globulin, being negatively charged at this pH passes into anode channel 20. Gamma 1 globulin passes directly through central channel since it has no net charge. Gamma 2 globulin, being positively charged at this pH, passes into cathode channel 21. All three streams are each combined with a color developing reagent 25 in mixing coils 11 and pass through optical detecting means 26 to measure amount of color which is related to concentration of protein. Seventh and eighth streams not shown may combine buffers 52 and 56 with color reagent 25 in mixing coils and later pass through optical detection means to provide reagent blank values to aid in computation of results. Connecting means not shown connect optical detecting means to data processing and display means 32 and 33 wherein signals from detection means are used to compute and display results of the measurement automatically. Optical detectors are indicated as individual filtered light sources 27. Transparent cells 58 and light sensors 28. A second filter may be employed between sample and sensor for fluorescence detection. Any of the optical density or fluoresent detectors well known in the art may be used or a single intergrated multipath detector may be employed. In an alternate embodiment not shown, liquid streams may be joined by an air stream. Air introduced concomitantly with the flow of liquids divides the liquid stream into a segmented liquid stream composed of alternate segments of liquid and air. In the course of travel of this stream, the segments of air and the surface tension of the air/liquid interfaces displace liquid from the inner surface of the fluid channel so as to prevent or substantially reduce the mixing of the samples with each other and hence prevent or reduce the contamination of one sample by another in the operation of the invention for analyzing a series of samples or standards.

Figure 6A:
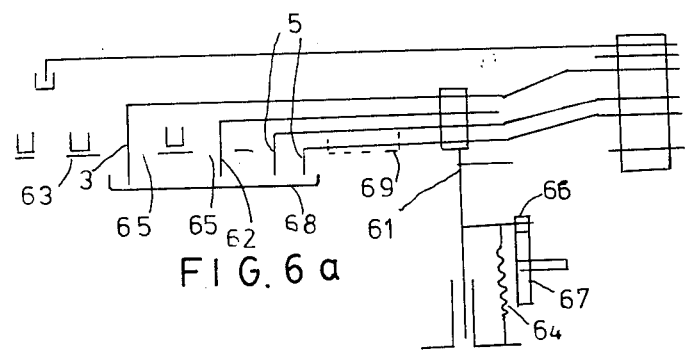
Figure 6B:
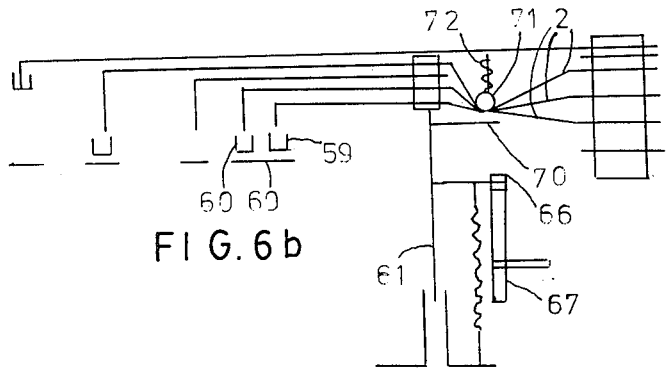

Now referring to the schematic diagram of a competitive binding analyzer of FIG. 6. Competitive binding analysis is carried out by the addition of labeled ligand 59 and specific binding agent 60 to each sample or standard 10. Peristaltic proportioning pump 1 pulls fluid at precise rates through flexible tubing lines 2, metering the fluids. Three of these lines terminate in sample pipet 3 and two reagent pipets 5. Pipet support means 61 holds these three pipets in position such that they are immersed in their respective liquids for a precise time interval. Level sensing finger 62 is fixed to support 61. This rests upon sample support means 63 and prevents pipets being pulled to a lower level by tension spring 64. This defines the middle of three levels at which pipets operate. A second operating position of pipets is shown in FIG. 6a. Rotation or translation of sample support 63 has aligned hole 65 in the support with level sensing finger 62 allowing it to penetrate. Spring 64 pulls pipet support 61 to a lower level at which cam follower 66 impinges on surface of drive cam 67. In this position, sample pipet 3 passes through a hole 65 between samples in sample support 63. Sample pipet 3 and reagent pipets 5 are now immersed in an aspirating wash or spacer liquid from wash liquid container 68 at a level beneath sample and reagent level. Reagents 60 and 59 have been displaced laterally out of the way of pipets 5 by movement of reagent support 69. FIG. 1b shows the third operating level of the pipets when cam 67 forces cam follower 66 and pipet support 61 to such a high level that the pipet tips clear the tops of the sample and reagent containers while these containers move. In this clearance position, compression bar 70 on pipet support 61 forces flexible tubes 2 against anvil 71 compressing springs 72 and pinching the tubes 2 closed. Occlusion of tubes causes vacuum to form in pump lines. When pipets are abruptly returned to liquid by action of spring 64, a rapid liquid flow occurs until vacuum is dissipated. This reduces volume of air aspirated into liquid lines during sample changing and increases throughput. Returning to FIG. 6, the three liquid streams are joined by a fourth fluid stream pumping gas, usually air. The air is introduced via line 73 and flows with liquids into confluent line 78 to mixer 11 and incubator 74. Mixer 11 usually consists of a coiled tube with the coils running vertically. The incubator is an elongate coiled tube that may be surrounded by a controlled temperature. The air introduced concomitantly with the flow of liquids divides the fluid stream into a segment fluid stream composed of alternate segments of liquid and air. In the course of travel of this stream, the segments of air and the surface tension of the air/liquid interfaces displace liquid from the inner surface of the tube or other fluid channel so as to prevent or substantially reduce the mixing of the samples with each other and hence prevent or reduce the contamination of one sample by another in the operation of the machine for analyzing a series of samples or standards. After thorough mixing of the three liquids and incubation to allow time for binding agent to combine at least partially with labeled and unlabeled ligand, the stream passes to separation module 13 where free ligand will be removed from the stream leaving the bound ligand in the stream for subsequent measurement. It should be noted that the dynamic, continuous nature and precise, reproducible timing of this system allow analysis with incomplete reaction of ligand and binding agent. When standards and unknowns receive identical treatment, the separation step may be performed many hours before equilibrium is reached and yield valid results. Incubated, segmented liquid stream enters central channel 12 of separator 13. Recipient liquid streams are pumped from containers 7 through upper channel 20 and lower channel 21. A difference of electric potential is applied between electrodes 50 and 51 within channels 20 and 21 respectively. Materials with net positive charge are acelerated toward cathode 51 in lower channel and materials with net negative charge are accelerated toward anode 50 in upper channel. Small molecules will move faster than large molecules. Highly charged molecules will move faster than lesser charged molecules. The semipermeable membranes 14 and 15 separating channel 12 from channels 20 and 21 are selected of a pore size to allow ready passage of the smaller unbound ligand and may retard passage of the larger, bound ligand, Millipore Filter Corp. markets a selection of suitable membranes with a choice of pore sizes. By pumping much greater volumes of liquid through recipient channels, unbound ligand reaching recipient channels is swept away before it can diffuse back into central channel. The recipient streams provide a surplus of ions to replace any lost from the central channel. This tends to maintain the acidity and ionic strength of the mixture within the central channel. It is important to avoid perturbation of its composition that might alter the binding phenomena. Recipient liquid streams leaving separator at outlets 47 and 49 are sent to waste w. Liquid in central channel, divested of its unbound ligand is now forced through optical detector 26 into four position rotary valve 75. A light absorbing agent of such nature as to remain within the central channel, is added to either one of the reagents or the wash liquid. The light absorbing agent may be fluorescent, in which case the emitted light may be detected. A large molecular weight, low net charge, water soluble, inert compound such as Blue Dextran 2000, a product of Pharmacia Fine Chemicals Corp., may be used. The system will operate with the color in either reagent or wash stream with a simple change in switching signals. The colored agent may be chemically incorporated into the binding agent. This has the added advantage of increasing the difference in size and change between bound and unbound ligand. The following describes operation when color is in reagent mixture. This will remain with bound ligand in the central channel and pass through optical detector 26. The optical detector senses the presence or absence of the colored agent. In this case it is wired to send a switching command to 4 position rotary valve 75 whenever the color of the solution disappears. To prevent false triggering by air segments, a time delay is built in, requiring continued absence of color for a time longer than an air segment would cause. Liquid flows into central port of valve and out of one of the four exit ports to a coil 76 in one of the four radioactivity measuring devices 77. A suitable electrically operated valve is marketed by the Hamilton Company. The time delay of the signal from the optical detector is set long enough for the interface between reagent and wash liquid to enter the coil 76 before the valve 75 switches. The coil 76 in radioactivity measuring device 77 is large enough so that the entire colored reagent segment is contained therein. Upon switching, the entire colored segment containing the bound labeled ligand is trapped within the sensitive volume of the measuring device for a static measurement for a fixed time interval which is initiated by the same signal. While the next coil in sequence is being flushed and filled, the measuring continues. At the end of the measuring interval, the accumulated measurement is transmitted to the data processor and recorder module 32 and the device 77 is reset and ready for the next refill. After 3 more reagent segments have been inserted in turn in the other coils, the valve will again switch to this coil and spacer fluid will first wash out the old specimen to waste until a new colored specimen fills and is trapped in the coil. The air segments in the measuring coils do not interfere with measurement. In continuous analysis, Habig, R. L. Clin. Chem. 15,1045,1969, demonstrated that retaining air segmentation throughout can reduce cross contamination to such an extent that throughput (samples/minute) can be considerably increased. If a new sample or standard is picked up every fifteen seconds, this system allows measuring intervals of at least 55 seconds while maintaining a throughput of 4 samples/minute. The nature of radioactive analysis requires a static measurement of almost a minute. This has limited the throughput of many present automatic radioimmunoassay systems. The present invention overcomes this limitation by freeing the processing of specimens from the measurement of radioactivity. Prior to the analysis of samples and standards, four identical specimens would ordinarily be entered into the system. These would eventually fill the 4 measuring devices 77 and the results of their measurement would be entered in processor 32. Any differences in values can be used to correct subsequent data for inequalities in sensitivity of the four detectors. Processor 32 may contain a modest computer for making such correction, formulation of standard relationships and calculation of concentrations of samples.

While I have shown and described the preferred embodiments of my invention, it will be understood that the invention may be embodied otherwise than as herein specifically illustrated or described, and that certain changes in the form and arrangement of parts and in the specific manner of practicing the invention may be made without departing from the underlying ideas or principles of this invention within the scope of the appended claims.

What is claimed is:

1. Apparatus for separating certain molecules from other molecules in a fluid, comprising: first and second members, each having a surface with groove means therein, said groove means having fluid inlet and outlet means; electrode means in said groove means; an inner member having slot means, said slot means having fluid inlet and outlet means; mounting means for mounting said first and said inner members in confronting face to face relation with said groove means in registry with said slot means, and for mounting said second and said inner members in confronting face to face relation with said groove means in registry with said slot means at another face of said inner member; permeable membrane means interposed between said first and said inner members and permeable membrane means interposed between said second and said inner members, so as to form three fluid channels with common permeable walls between said channels; and means for applying electrical potential between said electrode means.

2. Apparatus of claim 1, wherein no inner member is provided; said first member is mounted in confronting face to face relation with said second member with said groove means in registry with one another; and permeable membrane means interposed between said members so as to form two fluid channels with a common permeable wall therebetween.

3. Apparatus of claim 1, which further comprises: a plurality of inner members with slot means mounted in registry; a plurality of permeable membrane means interposed between individual inner members and between outermost of said inner members and said first and second members so as to form a plurality of fluid channels with common walls therebetween.

4. Apparatus of claim 1, wherein said groove means is formed by a combination of a separate slotted member applied to a flat member.

5. Apparatus for electrically separating certain particular types of molecules in a continuously moving fluid stream from other constituents of said fluid for subsequent analysis comprising: a central channel means through which flows a fluid mixture to be separated for analysis; at least one additional parallel recipient flow channel means adjacent said central channel and separated therefrom along its length by membrane means, said membrane means being sufficiently permeable to allow passage of at least one of the types of molecules to be separated; electrode means in at least two of said channels; electrical means for applying a difference of electrical potential across said electrode means, said potential applying a driving force to move certain molecules, having a net electrical charge, across said membrane means, thereby moving certain molecules from the fluid moving in one channel into the fluid moving in another channel.

6. Apparatus of claim 5 further comprising: analytical measurement means disposed so as to measure the composition of the separated fluid in at least one of the channels leaving the electrical field.

7. Apparatus of claim 5, wherein the distance between channels is short relative to the length of said channels, providing a short exit path for migrating molecules and a relatively long exposure to the electrical force.

8. Apparatus of claim 5, further comprising: analytical measuring means disposed so as to measure the concentration of a component of the separated fluid in at least one of the channels after leaving said electrical field means.

9. Apparatus of claim 5, further comprising: means for separating a succession of sample solutions by spacer liquid segments in said fluid stream to reduce contamination between samples.

10. Apparatus of claim 5, further comprising: means for incorporating gas segments in said fluid stream to reduce contamination between samples.

11. A method of electrical separation of molecules in a continuously flowing fluid stream for analysis which includes the steps of:
 (1) Passing a sample solution mixture through a first elongate fluid flow channel;
 (2) Passing at least one other fluid through at least one other elongate fluid flow channel adjacent said first channel and separated therefrom by permeable membrane means;
 (3) Applying electrical field means across said channels in a direction transverse to the direction of fluid flow to cause migration of certain electrically charged fluid components across said membrane means into another separate moving fluid stream in another said channel;
 (4) Providing a short exit path for electrically migrating components and a relatively long path for exposure to said electrical field.

12. The method of claim 11, including passing a succession of sample mixtures separated by spacer liquid segments through said first elongate fluid flow channel to reduce contamination between samples.

13. The method of claim 11, including incorporating gas segments in said fluid stream to reduce contamination between successive samples.

14. The method of claim 11, including using a membrane of a pore size to selectively inhibit the movement of larger components of said sample solution mixture therethrough while not inhibiting the movement of smaller components.

15. Apparatus for electrically separating certain types of molecules in a moving fluid from other constituents of said fluid for subsequent analysis comprising: first and second members, each having a surface with groove means therein, said groove means having fluid inlet and outlet means; electrode means in said groove means; an inner member having slot means, said slot means having fluid inlet and outlet means; mounting means for mounting said first and said inner member in confronting face to face relation with said groove means in registry with said slot means, and for mounting said second and said inner member in confronting face to face relation with said groove means in registry with said slot means at another face of said inner member; permeable membrane means interposed between said first and said inner member and permeable membrane means interposed between said second and said inner member, so as to form three fluid channels with common permeable walls between said channels; said moving fluid flowing through one of said channels via said inlet and outlet means; other fluid moving through other of said channels via said inlet and outlet means; said molecule having a net electrical charge, being driven across said membrane means by electrical potential applied across said electrode means, thereby moving said molecules from the fluid in one channel into the fluid moving in another channel.

16. Apparatus for electrically separating molecules in a moving fluid from other constituents of said fluid for subsequent analysis comprising: first and second member means each having a surface with groove means therein, said groove means having fluid inlet and outlet means; electrode means in said groove means; said first member means mounted in confronting face to face relation with said second member means, with said groove means in registry with one another; and permeable membrane means interposed between said member means so as to form two fluid channels with a common permeable wall therebetween.

17. Apparatus of claim 15, which further comprises: a plurality of inner members with slot means mounted in registry; a plurality of permeable membrane means interposed between individual inner members and between outermost of said inner members and said first and second members so as to form a plurality of fluid channels with common walls therebetween.

18. Apparatus of claim 15, wherein said groove means is formed by a combination of a separate slotted member applied to a flat member.

* * * * *